(12) United States Patent
Bohm et al.

(10) Patent No.: US 7,665,303 B2
(45) Date of Patent: *Feb. 23, 2010

(54) METHOD OF SEGREGATING A BOLUS OF FLUID USING A PNEUMATIC ACTUATOR IN A FLUID HANDLING CIRCUIT

(75) Inventors: Sebastian Bohm, Los Gatos, CA (US); Alan W. McNeilage, Inverness (GB)

(73) Assignee: LifeScan Scotland, Ltd.

( * ) Notice: Subject to any disclaimer, the term of this patent is extended or adjusted under 35 U.S.C. 154(b) by 829 days.

This patent is subject to a terminal disclaimer.

(21) Appl. No.: 11/095,636

(22) Filed: Mar. 30, 2005

(65) Prior Publication Data
US 2005/0220629 A1 Oct. 6, 2005

Related U.S. Application Data

(60) Provisional application No. 60/558,390, filed on Mar. 31, 2004, provisional application No. 60/558,375, filed on Mar. 31, 2004.

(51) Int. Cl.
*F01K 1/00* (2006.01)
(52) U.S. Cl. .......................... 60/643; 60/645
(58) Field of Classification Search ............... 60/643, 60/645, 646, 657
See application file for complete search history.

(56) References Cited

U.S. PATENT DOCUMENTS

| | | | |
|---|---|---|---|
| 3,799,742 A | 3/1974 | Coleman | |
| 4,676,274 A | 6/1987 | Brown | |
| 4,963,498 A | 10/1990 | Hillman et al. | |
| 5,223,226 A | * | 6/1993 | Wittmer et al. ............. 422/100 |
| 5,660,993 A | 8/1997 | Cathey et al. | |
| 5,922,591 A | 7/1999 | Anderson et al. | |
| 6,130,098 A | 10/2000 | Handique et al. | |
| 6,143,248 A | 11/2000 | Kellogg et al. | |
| 6,296,020 B1 | 10/2001 | McNeely et al. | |
| 6,326,211 B1 | 12/2001 | Anderson et al. | |
| 6,360,775 B1 | 3/2002 | Barth et al. | |

(Continued)

FOREIGN PATENT DOCUMENTS

WO    WO 97/21090    6/1997

(Continued)

OTHER PUBLICATIONS

U.S. Appl. No. 10/811,446, filed Mar. 26, 2004.

(Continued)

*Primary Examiner*—Hoang M Nguyen

(57) ABSTRACT

The invention described is a method of segregating a bolus of fluid using a pneumatic actuator in a fluid handling circuit. The described invention further includes a method of segregating a bolus of fluid using a pneumatic actuator in a fluid handling circuit wherein the method includes the step of injecting an air pocket into the fluid stream to create the bolus. In addition, the described invention includes a method of measuring the analyte concentration in a bolus of fluid using a pneumatic actuator in a fluid handling circuit. The described invention further includes a method of measuring the analyte concentration in a bolus of fluid using a pneumatic actuator in a fluid handling circuit wherein the method includes the step of injecting an air pocket into the fluid stream to create the bolus.

4 Claims, 4 Drawing Sheets

U.S. PATENT DOCUMENTS

| | | | |
|---|---|---|---|
| 6,481,453 | B1 | 11/2002 | O'Connor et al. |
| 6,852,287 | B2 * | 2/2005 | Ganesan ..................... 422/99 |
| 6,866,762 | B2 * | 3/2005 | Gascoyne et al. ........... 204/547 |
| 6,866,822 | B1 | 3/2005 | House et al. |
| 6,893,547 | B2 * | 5/2005 | Gascoyne et al. ........... 204/547 |
| 6,990,849 | B2 | 1/2006 | Bohm et al. |
| 7,059,352 | B2 | 6/2006 | Bohm |
| 2002/0114738 | A1 | 8/2002 | Wyzgol et al. |
| 2002/0141903 | A1 | 10/2002 | Parunak et al. |
| 2002/0143437 | A1 | 10/2002 | Handique et al. |
| 2003/0070677 | A1 | 4/2003 | Handique et al. |
| 2003/0196714 | A1 | 10/2003 | Gilbert et al. |
| 2004/0072357 | A1 * | 4/2004 | Stiene et al. ................ 436/69 |
| 2004/0096959 | A1 | 5/2004 | Stiene et al. |
| 2004/0099321 | A1 | 5/2004 | Schoeniger et al. |
| 2004/0109790 | A1 | 6/2004 | Shartle et al. |
| 2006/0002817 | A1 | 1/2006 | Bohm et al. |

FOREIGN PATENT DOCUMENTS

| | | |
|---|---|---|
| WO | WO 00/22436 | 4/2000 |
| WO | WO 01/78893 A2 | 10/2001 |
| WO | WO 01/88525 | 11/2001 |
| WO | WO 01/90614 A2 | 11/2001 |
| WO | WO 02/07884 | 1/2002 |
| WO | WO 02/41995 | 5/2002 |
| WO | WO 02/42650 | 5/2002 |
| WO | WO 02/49507 A1 | 6/2002 |
| WO | WO 02/078845 | 10/2002 |
| WO | WO 03/012406 | 2/2003 |

OTHER PUBLICATIONS

U.S. Appl. No. 10/883,585, filed Jun. 30, 2004.

Jun Zeng, et al., "Fluidic Capacitance Model of Capillary-Driven Stop Valves" ASME 2000, Microcosm Technologies, Inc., Cambridge, MA 02142, pp. 1-7.

Richard M. Moroney, et al., "A Passive Fluid Valve Element for a High-density Chemical Synthesis Machine", Sarnoff Corporation CN-5300, Princeton, NJ 08543, pp. 1-4.

P.F. Man, et al., "Microfabricated Capillary-Driven Stop Valve and Sample Injector" MEMS 98, Jan. 25-29, 1998, Heidelberg, Germany, pp. 45-50, 1998 IEEE.

Brett R. Wenner, et al., "Biosensing on the CD Microfluidic Platform with Genetically Engineered Proteins", 2000 Society of Automotive Engineers, Inc., pp. 1-6, 2000-01-2513.

Marc J. Madou, et al., "Design and Fabrication of CD-like Microfluidic Platforms for Diagnostics: Microfluidic Functions", Biomedical Microdevices 3:3, 245-254, 2001 Kluwer Academic Publishers, Manufactured in the Netherlands.

K. Handique, et al., "On-Chip Thermopneumatic Pressure for Discrete Drop Pumping", Analytical Chemistry, vol. 73, No. 8, Apr. 15, 2001, The University of Michigan, Ann Arbor, Michigan 48109-2136, pp. 1831-1838.

K. Handique, et al., "Nanoliter Liquid Metering in Microchannels Using Hydrophobic Patterns", Analytical Chemical Society Pub. On Web Aug. 3, 2000, The University of Michigan, Ann Arbor, Michigan 48109-2136, pp. 4100-4109, No. 72.

* cited by examiner

METHOD OF SEGREGATING A BOLUS OF FLUID USING A PNEUMATIC ACTUATOR IN A FLUID HANDLING CIRCUIT

CROSS-REFERENCE

This application claims the benefit of U.S. Provisional Application No. 60/558,390, filed Mar. 31, 2004, which application is incorporated herein by reference. This application claims the benefit of U.S. Provisional Application No. 60/558,375, filed Mar. 31, 2004, which application is incorporated herein by reference.

This application is related to the following copending patent applications: application Ser. No. 11/096,036; and application Ser. No. 11/096,005; and application Ser. No. 11/095,035; and application Ser. No. 11/095,374; and application Ser. No. 11/095,635; which are hereby incorporated herein by reference.

FIELD OF THE INVENTION

The present invention relates, in general, to a method of segregating a bolus of fluid using a pneumatic actuator in a fluid handling circuit and, more particularly, to a method of segregating a bolus of fluid using a pneumatic actuator in a fluid handling circuit wherein the method includes the step of injecting an air pocket into the fluid stream to create the bolus. Further, the present invention relates, in general, to a method of measuring the analyte concentration in a bolus of fluid using a pneumatic actuator in a fluid handling circuit and, more particularly, to a method of measuring the analyte concentration in a bolus of fluid using a pneumatic actuator in a fluid handling circuit wherein the method includes the step of injecting an air pocket into the fluid stream to create the bolus.

SUMMARY OF THE INVENTION

The present invention is directed to a method of segregating a bolus of fluid using a pneumatic actuator in a fluid handling circuit. In one embodiment of a method of segregating a bolus of fluid using a pneumatic actuator in a fluid handling circuit according to the present invention the method includes the steps of moving a fluid into a first end of a channel in the fluid handling circuit, injecting an air pocket from the pneumatic actuator into the channel when the fluid reaches a fill detector in the channel, the air pocket being injected upstream from the fill detector, forming a bolus of fluid extending from the fill detector to the air pocket and forcing the fluid bolus and the gas pocket through the channel until the gas pocket reaches a vent. In a further embodiment of a method of segregating a bolus of fluid using a pneumatic actuator in a fluid handling circuit the pneumatic actuator includes a controller, a pressure generator connected to the controller and an isolator for isolating the pressure generator from the channel. In a further embodiment of a method of segregating a bolus of fluid using a pneumatic actuator in a fluid handling circuit, the pneumatic actuator further includes a gas pocket connected to the channel through the isolator and a heater controlled by the controller wherein the heater is adapted to heat gas in the gas pocket. In a further embodiment of a method of segregating a bolus of fluid using a pneumatic actuator in a fluid handling circuit the pneumatic actuator further includes a gas pocket connected to the channel by the isolator, a flexible bladder connected to the gas pocket and a plunger connected to the flexible bladder, the plunger being controlled by the controller.

The present invention is also directed to a method of measuring the analyte concentration in a bolus of fluid using a pneumatic actuator in a fluid handling circuit, the method including the steps of positioning the fluid in a channel in the fluid handling circuit, actuating the pneumatic actuator to inject an air into the channel when the fluid is detected by a fill detector, injecting air from the pneumatic actuator into the channel to form an air pocket upstream from the fill detector, forming a bolus of the fluid, the bolus having a length which is substantially equal to the distance from the fill detector to the pneumatic actuator, moving the bolus and the air pocket through the channel until the fluid is positioned over an analyte detector in the channel, measuring the analyte content of the bolus and venting the air pocket from the channel. In a further embodiment of a method of segregating a bolus of fluid using a pneumatic actuator in a fluid handling circuit the pneumatic actuator includes a controller and a pressure generator connected to the controller and an isolator for isolating the pressure generator from the channel. In a further embodiment of a method of segregating a bolus of fluid using a pneumatic actuator in a fluid handling circuit the pneumatic actuator further includes a gas pocket connected to the channel through the isolator, a heater controlled by the controller and adapted to heat gas in the gas pocket. In a further embodiment of a method of segregating a bolus of fluid using a pneumatic actuator in a fluid handling circuit the pneumatic actuator further includes a gas pocket connected to the channel by the isolator, a flexible bladder connected to the gas pocket and a plunger connected to the flexible bladder, the plunger being controlled by the controller.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
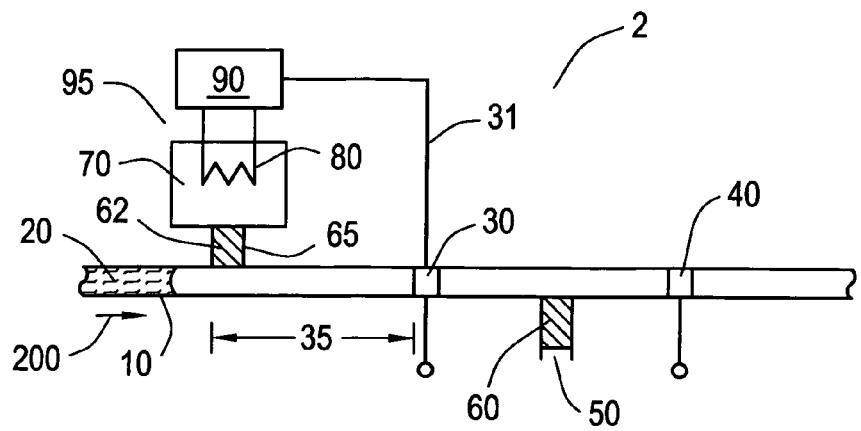
FIG. 1 is a schematic illustration of sample liquid entering a pneumatic liquid handling circuit, according to one embodiment of the present invention.
Figure 8:
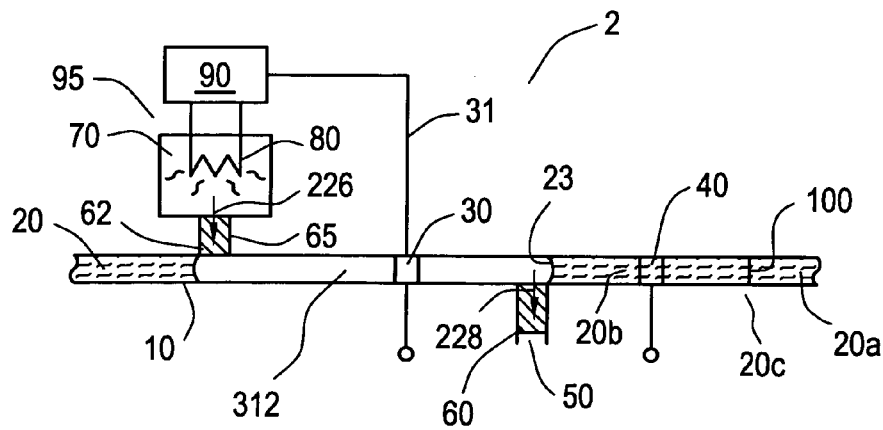
FIG. 8 is a schematic illustration of combined sample bolus positioning in the pneumatic liquid handling circuit of FIG. 1.
Figure 9:
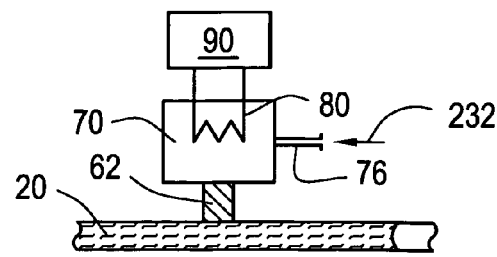
FIG. 9 is an illustration of an alternative embodiment of the pneumatic liquid handling circuit of FIG. 1.
Figure 10:
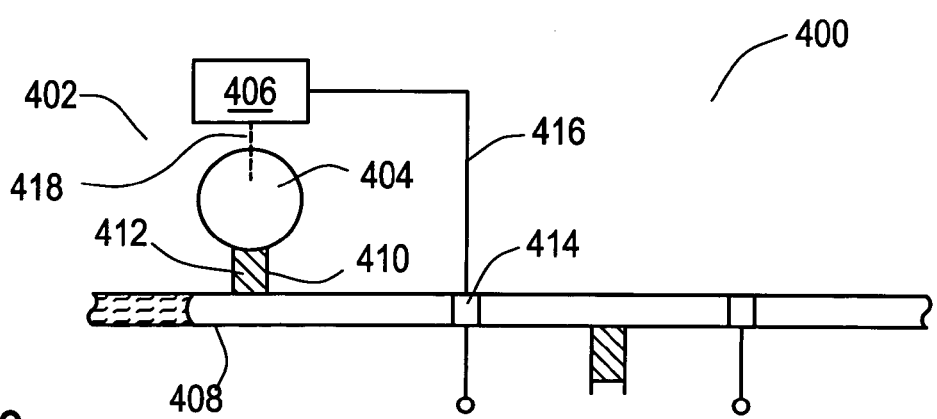
FIG. 10 is a schematic illustration of a bladder-containing pneumatic liquid handling circuit.

FIG. 1 is a schematic illustration of a pneumatic liquid handling circuit, according to an embodiment of the present invention. FIGS. 2 through 8 illustrate flow of sample liquid through the pneumatic liquid handling circuit of FIG. 1. FIG. 9 is an illustration of an alternative embodiment of the pneumatic liquid handling circuit of FIG. 1. FIG. 10 is a schematic illustration of a bladder-containing pneumatic liquid handling circuit.

The pneumatic liquid handling circuits illustrated in FIGS. 1 through 10 (which may also be referred to as fluid handling circuits including a pneumatic actuator) car be used to measure analyte in sample liquid. Sample liquid can be interstitial fluid, whole blood, or plasma. Flow into pneumatic liquid handling circuits can be driven by capillary, gravitational, and centrifugal forces. Flow into pneumatic liquid handling circuits can also be driven by pressurized gas, pumps, or by pressure at the source of sample liquid. Flow channels in pneumatic liquid handling circuits can be rectangular, square, or semicircular in cross section, although most preferably flow channels are rectangular in cross section, making them easier to manufacture. The length, width, and depth of flow channels vary, but are generally on the order of 25 to 2500 microns, and are often 500 microns or less. Pneumatic liquid handling circuits can be constructed using laminated layers of plastic, bonded with adhesive, or can be injection molded plastic. Suitable plastics include polyester, polycarbonate, acrylic, polystyrene, polyolefins, polyimides, and any other thermoplastic polymers. Pneumatic liquid handling circuits may also be constructed using etched silicon or glass.

FIG. 1 is a schematic illustration of sample liquid 20 entering pneumatic liquid handling circuit 2 in the direction of arrow 200, according to an embodiment of the present invention. Pneumatic liquid handling circuit 2 includes main channel 10, in which sample liquid 20 flows from left to right. Fill detector 30, located within main channel 10, is used to detect the presence of sample liquid 20. Pneumatic actuator 95 includes gas pocket 70, heater 80, and controller 90. Gas pocket 70 is connected to main channel 10 by way of first branching channel 65. First branching channel 65 includes first hydrophobic area 62. First hydrophobic area 62 prevents sample liquid 20 from flowing into gas pocket 70, for reasons explained below. When multiplied by the cross sectional area of main channel 10, measured distance 35 defines a fixed volume within main channel 10, between branching channel 65 and fill detector 30. Pneumatic liquid handling circuit 2 includes vent 50. Gas flows through vent 50, but sample liquid 20 does not. Vent 50 branches from main channel 10, and includes second hydrophobic area 60. Pneumatic liquid handling circuit 2 includes analyte sensor 40, located down stream of vent 50. Analyte sensor 40 is used to determine analyte concentration in sample liquid 20.

In a preferred embodiment, analyte sensor 40 measures glucose, and sample liquid 20 is interstitial fluid. When measuring glucose, analyte sensor 40 can contain a redox reagent system that includes an enzyme and redox active compounds or mediators. A variety of mediators are known in the art, such as ferricyanide, phenazine ethosulphate, phenazine methosulfate, phenylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, and ruthenium complexes. Suitable enzymes include glucose oxidase and dehydrogenase (both NAD and PQQ based). Other substances that may be present in a redox reagent system include buffering agents (e.g., citraconate, citrate, malic, maleic, and phosphate buffers); divalent cations (e.g., calcium chloride, and magnesium chloride); surfactants (e.g., Triton, Macol, Tetronic, Silwet, Zonyl, and Pluronic); and stabilizing agents (e.g., albumin, sucrose, trehalose, mannitol and lactose). Other analytes and indicators which can be measured in the system of the present invention include urea, hemoglobin, lactate, alcohol, cholesterol, amino acids, choline, and coagulation factors.

Hydrophobic areas 60 and 62 allow air to pass, but not liquid. This is because hydrophobic areas 60 and 62 repel aqueous samples, such as interstitial fluid, blood, and plasma. For flow of aqueous sample to occur beyond hydrophobic areas 60 and 62, the pressure of sample liquid 20 must exceed the burst pressures of the hydrophobic areas 60 and 62. Burst pressure is determined by channel geometry, physical properties of the channels surface, and physical properties of sample liquid 20. In designing pneumatic liquid handling circuit 2, burst pressures can be selected that prevent flow of sample liquid 20 beyond hydrophobic areas 60 and 62. Hydrophobic areas 60 and 62 may also be referred to as an insulator since hydrophobic area 62 insulates gas pocket 70 from the fluid in main channel 10 and channel 50 from the fluid in main channel 10 but allows air to pass out of gas pocket 70 and into channel 50. A structural passive valve useable as an insulator or in place of hydrophobic areas 60 or 62 may also be formed by a sudden widening in the channel (e.g. a widening in channel 65 if used to replace hydrophobic area 62 or a widening in channel 50 if used to replace hydrophobic area 60) such that when a liquid front reaches the sudden widening, a meniscus is formed at the point of the widening (angle preferable more acute than 90 degrees. In order for the liquid to move into the wider section of the channel, the liquid needs to be pressurized so that the meniscus is pushed around the edge thereby wetting the wider area. This requires, as with the hydrophobic based passive valve, a minimum pressure which is referred to as burst pressure.

In fabricating hydrophobic areas 60 and 62, at least one side of the flow channel is rendered hydrophobic. This can be accomplished using commercially available hydrophobic inks, and various printing techniques including screen printing, gravure, slot coating, flexo, offset, and spray coating. For example, the ink FluoroPel PFC MH can be used to form hydrophobic areas 60 and 62. FluoroPel PFC MH can be purchased from Cytonix Inc., of Beltsville, Md.

When characterizing the wettability of a surface, its contact angle with water is often measured. To do this, a drop of water is placed onto the surface, and the angle is measured between the surface and a line drawn tangent to the liquid drop. As a point of reference, completely hydrophobic material has a contact angle with water of 180 degrees, while untreated polyester typically has a contact angle of approximately 70 degrees. Hydrophilic surfaces can have a contact angle as low as 0 degrees. In this invention, hydrophobic areas typically have a contact angle of between 70 and 180 degrees, while hydrophilic areas typically have a contact angle of between 0 and 70 degrees. When screen printed onto polyester, FluoroPel PFC MH forms a hydrophobic area having a contact angle with water of approximately 150 degrees.

Cytonix offers hydrophobic ink formulations that have been optimized for use with other types of printing, such as flexo and offset, as well as spray coating. Hydrophobic inks such as those used in printing microscope slides are also suitable for use in printing hydrophobic areas. Alternatively, commercially available screen printing inks can be modified for use in printing hydrophobic areas. For example, Zonyl fluoroadditives, sold by DuPont Corporation of Delaware, can be used as an additive to traditional screen printing inks.

Figure 2:
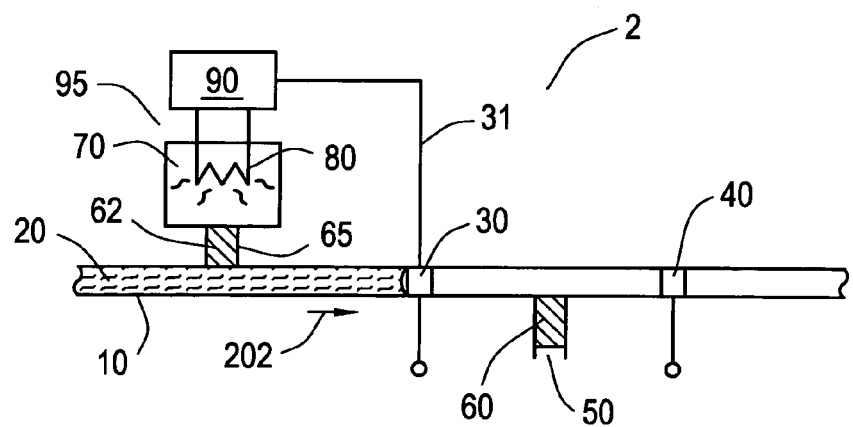
FIG. 2 is a schematic illustration of sample liquid reaching a fill detector in the pneumatic liquid handling circuit of FIG. 1.

FIG. 2 is a schematic illustration of sample liquid 20 flowing in the direction of arrow 202 and reaching fill detector 30. Fill detector 30 detects the presence of sample liquid 20 using various methods. For example, fill detector 30 can include electrodes for measuring conductivity and/or capacitance of sample liquid 20. Alternatively, fill detector 30 can be optical, and detect sample by measuring a change in optical properties when sample liquid 20 reaches fill detector 30. Further details in regard to fill detectors suitable for use in devices according to the present invention are included in U.S. patent application Ser. No. 10/811,446 filed on Mar. 26, 2004, which is hereby incorporated by reference.

Figure 3:
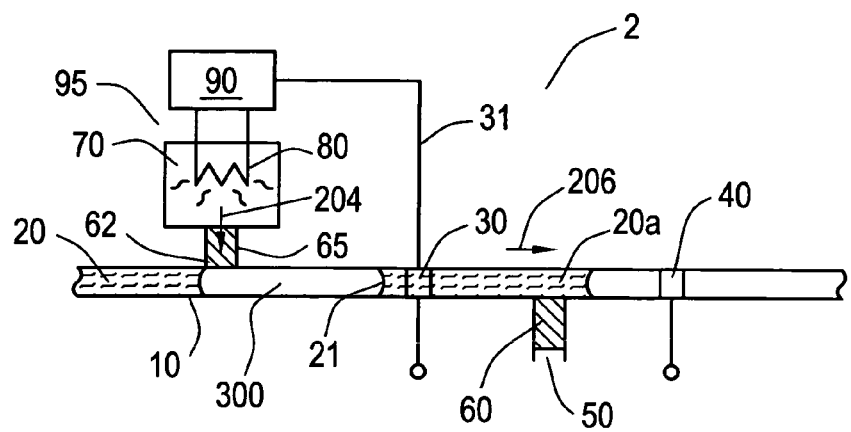
FIG. 3 is a schematic illustration of first sample bolus formation in the pneumatic liquid handling circuit of FIG. 1.

Feedback loop 31 provides electronic connection between fill detector 30 and controller 90. As sample liquid 20 flows in the direction of arrow 202, and reaches fill detector 30, it is detected and pneumatic actuator 95 is activated by a signal from feedback loop 31. When pneumatic actuator 95 is activated, heater 80 turns on, heating the air in gas pocket 70. As illustrated in FIG. 3, air in gas pocket 70 expands as it is heated, expanding into branching channel 65 and main channel 10. Expanded air pocket 300 forms first sample bolus 20*a*, which may also be referred to as a sample plug, and forces first sample bolus 20*a* towards vent 50, in the direction of arrow 206. The volume of first sample bolus 20*a* is determined by multiplying measured distance 35 times the cross sectional area of main channel 10, as discussed in reference to FIG. 1.

Figure 4:
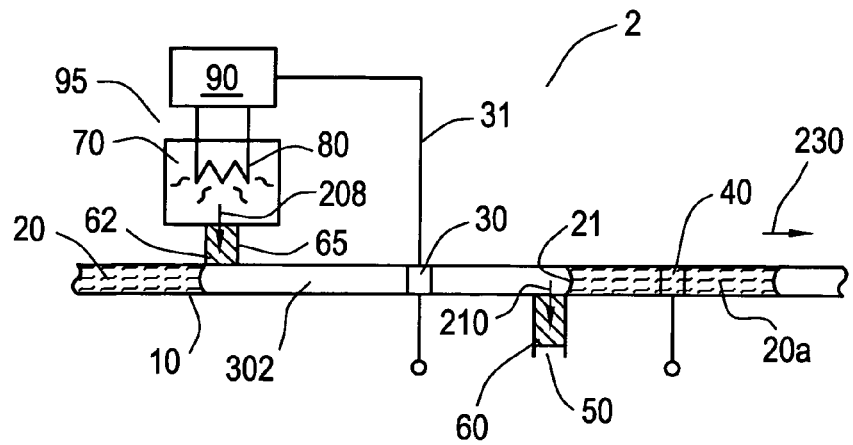
FIG. 4 is a schematic illustration of first sample bolus positioning in the pneumatic liquid handling circuit of FIG. 1.

As illustrated in FIG. 4, heater 80 continues to heat the air in gas pocket 70, causing the air to expand in the direction of arrow 208, and increasing the size of expanded air pocket 302. This causes first sample bolus 20*a* to move down main channel 10 in the direction of arrow 230. As the trailing edge 21 of first sample bolus 20*a* reaches vent 50, expanded air pocket 302 is vented to atmosphere by way of vent 50 in the direction of arrow 210. Movement of first sample bolus 20*a* in the direction of arrow 230 stops. Heater 80 is then turned off, and the air contained in gas pocket 70 and expanded air pocket 302 returns to ambient temperature and pressure. First sample bolus 20*a* stops because the pressure in main channel 10 is atmospheric on both sides of sample bolus 20*a*. The change in pressure to atmospheric is almost instantaneous, resulting in substantially immediate stabilization of first sample bolus 20*a*.

Various means can be used for determining when to turn off heater 80. This includes using a fixed time after first sample bolus 20*a* has been detected at analyte sensor 40, or by using a fixed time after first sample bolus 20*a* leaves contact with fill detector 30. In either case, heater 80 is turned off seconds after trailing edge 21 makes contact with vent 50.

While first sample bolus 20*a* is in contact with analyte sensor 40, various measurements can be made. This includes, for example, electrochemical determination of glucose concentration in bolus 20*a*. Measurements can be made while first sample bolus 20*a* is stationary, or while first sample bolus 20*a* is flowing over analyte sensor 40.

Figure 5:
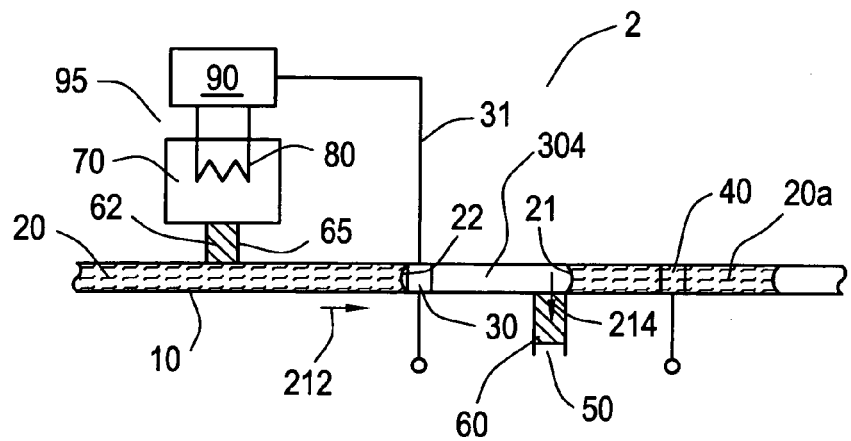
FIG. 5 is a schematic illustration of sample liquid flow in the pneumatic liquid handling circuit of FIG. 1.

The next step in the sequence is illustrated in FIG. 5. While measurements are made on first sample bolus 20*a* using analyte sensor 40, air pocket 304 remains at atmospheric pressure because it is in direct contact with the atmosphere by way of vent 50 in the direction of arrow 214. Sample liquid 20 flows in the direction of arrow 212, towards fill detector 30. As sample liquid 20 flows in the direction of arrow 212, air pocket 304 is vented by way of vent 50, leaving first sample bolus 20*a* stationary. Sample bolus 20*a* is stationary because the pressure on either side of sample bolus 20*a* is the same.

While sample liquid 20 flows in the direction of arrow 212, heater 80 is off, and the gas in gas pocket 70 cools. While the gas in gas pocket 70 cools, its pressure decreases, causing a pressure differential across first hydrophobic area 62. This can be undesirable, in that it provides a driving force for flow of sample liquid 20 into gas pocket 70. Flow of sample liquid 20 into gas pocket 70 could interfere with heater 80 in subsequent steps. Flow of sample liquid 20 into gas pocket 70 can be avoided using a variety of techniques. In one technique, first hydrophobic area 62 can be designed to have a burst pressure in excess of the pressure differential caused by cooling the gas in gas pocket 70. In this case, the decrease in pressure while the gas in gas pocket 70 cools is insufficient to cause sample liquid 20 to flow beyond first hydrophobic area 62. A second technique for preventing the flow of sample liquid 20 into gas pocket 70 is illustrated in FIG. 9. In this technique, gas pocket 70 is provided with gas pocket vent 76 that is always open to atmosphere. When sample liquid 20 flows in the direction of arrow 212, gas pocket 70 maintains direct contact with atmosphere by way of gas pocket vent 76. When heater 80 is turned off, and gas in gas pocket 70 cools, air is drawn into gas pocket 70 through gas pocket vent 76 in the direction of arrow 232, maintaining atmospheric pressure in gas pocket 70. This decreases the difference in pressure between sample liquid 20 and the gas in gas pocket 70, minimizing the driving force for flow of sample liquid 20 into gas pocket 70. When heating the gas in gas pocket 70, heater 80 can be driven with sufficient power to compensate for escape of gas by way of gas pocket vent 76, allowing the pressure of gas in gas pocket 70 to increase, as needed. In designing gas pocket vent 76, the resistance to flow in gas pocket vent 76 can be controlled. Two variables that effect the resistance to flow in gas pocket vent 76 are its cross sectional area and its length. Gas pocket vent 76 can be fabricated using laminates or injection molding, or with any of the techniques outlined earlier.

Figure 6:
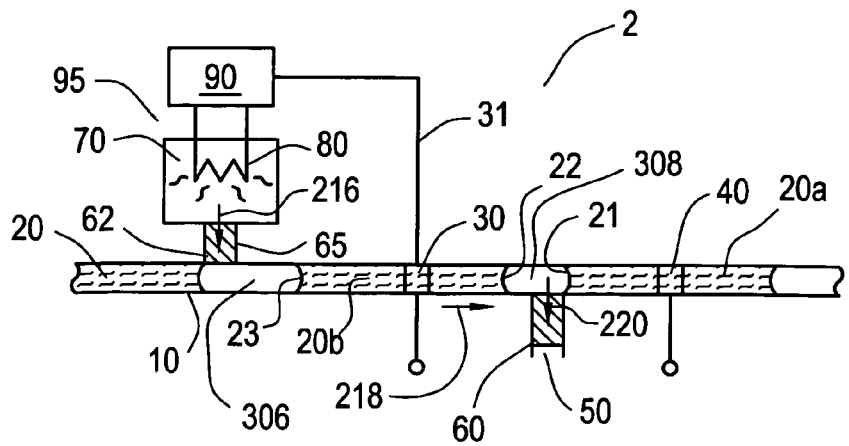
FIG. 6 is a schematic illustration of second sample bolus formation in the pneumatic liquid handling circuit of FIG. 1.

Returning to FIG. 5, as the leading edge 22 of sample liquid 20 reaches fill detector 30, a signal is sent to controller 90 by way of feedback loop 31. Heater 80 is activated, increasing the temperature and pressure of the air in gas pocket 70. As the air in gas pocket 70 expands, a second sample bolus 20*b* forms, as illustrated in FIG. 6. As the air in gas pocket 70 continues to expand, expanded air pocket 306 increases in size, forcing second sample bolus 20*b* to move in the direction of arrow 218, towards vent 50 and first sample bolus 20*a*. The air in air pocket 308 escapes through vent 50 in the direction of arrow 220. During this time, first sample bolus 20*a* remains stationary because the pressure on either side of it is the same.

Figure 7:
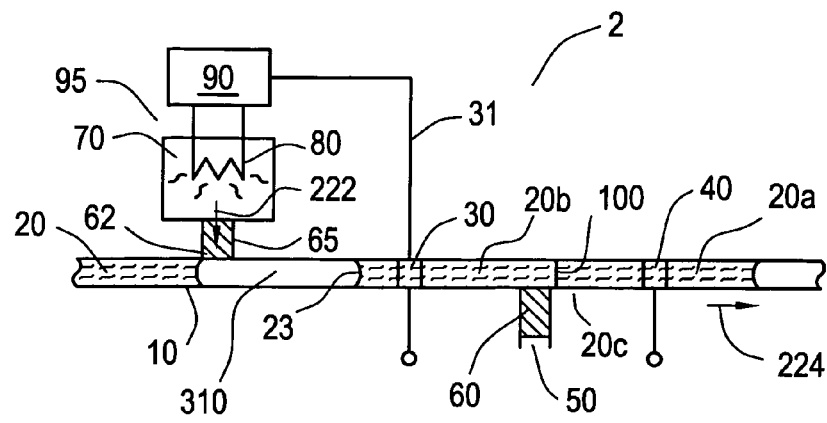
FIG. 7 is a schematic illustration of combined sample bolus formation in the pneumatic liquid handling circuit of FIG. 1.

In time, leading edge 22 of second sample bolus 20*b* reaches trailing edge 21 of first sample bolus 20*a*, and the bolus combine, forming combined sample bolus 20*c*, as illustrated in FIG. 7. The point at which first sample bolus 20*a* and second sample bolus 20*b* combine is indicated by label 100. Heater 80 continues to heat the air in gas pocket 70, increasing the size of expanded air pocket 310 and causing combined sample 20*c* to flow in the direction of arrow 224. Eventually, second trailing edge 23 reaches vent 50, as illustrated in FIG. 8.

As trailing edge 23 reaches vent 50, expanded air pocket 312 is vented to atmosphere by way of vent 50 in the direction of arrow 228. Since the pressure on both sides of combined sample bolus 20*c* are at atmospheric pressure, combined sample bolus 20*c* remains stationary. At this point, heater 80 is turned off, and sample liquid 20 flows into main channel 10, repeating the sequence outlined above.

While combined sample bolus 20*c* is stationary, a measurement can be made using analyte sensor 40. As indicated by label 100, the portion of sample in contact with analyte sensor 40 originates from second sample bolus 20*b*. As long as flow in main channel 10 remains laminar, measurement on a portion of combined sample bolus 20*c* originating from second sample bolus 20*b* is possible. Factors effecting laminar flow include the cross sectional area of main channel 10, the flow rate of combined sample bolus 20*c*, and the physical properties of combined sample bolus 20c. Measurements using analyte sensor 40 should be made within seconds after second trailing edge 23 reaches vent 50. This minimizes diffusion of analyte between portions from the first and second sample bolus.

In an alternative embodiment, a mechanical approach can be used to move sample liquid in a pneumatic liquid handling circuit. Instead of using a heater to generate pressure, a flexible bladder is used. An actuator compresses the bladder, generating pressure and causing flow. A bladder-containing pneumatic liquid handling circuit 400 is illustrated in FIG. 10. The procedure for using bladder-containing pneumatic liquid handling circuit 400 is identical to that used for the circuits illustrated in FIGS. 1 through 9 with the exception that an actuator and bladder is used instead of a heater.

A variety of bladder designs can be used. In some designs, a pocket is created, and at least one flexible cover is placed over the pocket. The pocket is directly connected to the flow channels, and, when squeezed, generates pressure that moves liquid. Covers can be fabricated using many materials, such as metals and plastics. A particularly suitable material includes thin polymer films, such as 0.004" thick polyester, polycarbonate, polyolefins, or acrylic. Elastomeric films can also be used. Pockets can be created using injection molded plastics, such as ABS, polycarbonate, or acrylics, or can be formed using die cut laminates.

Actuators for compressing a bladder can take many shapes. A particularly useful actuator includes the use of a solenoid coupled to a plunger. When energized, the solenoid moves a plunger that compresses the bladder. When the solenoid is de-energized, the bladder returns to its original shape. Solenoids and plungers are typically housed in an external device.

Further details in regard to bladders and actuators suitable for use in devices according to the present invention are included in U.S. patent application Ser. No. 10/666,846 filed on Sep. 18, 2004, and U.S. patent application Ser. No. 09/637,504 filed on Aug. 11, 2000, which are hereby incorporated by reference.

FIG. 10 is an illustration of a bladder-containing pneumatic liquid handling circuit 400. Bladder-containing pneumatic liquid handling circuit 400 includes main channel 408, in which sample liquid 420 flows. Fill detector 414, located within main channel 420, is used to detect sample liquid 420. Pneumatic actuator 402 includes plunger 418, solenoid 406. Bladder 404 is connected to main channel 408 by way of first branching channel 410. First branching channel 410 includes first hydrophobic area 412. First hydrophobic area 412 prevents sample liquid 420 from entering bladder 404. Feedback loop 416 provides electronic connection between fill detector 414 and solenoid 406. When sample liquid 420 reaches fill detector 414, it is detected, and solenoid 406 is activated by way of feedback loop 416. When solenoid 406 is activated, it causes plunger 418 to compress bladder 404 and displaces air within bladder 404, in the same way heater 80 causes displacement in the designs illustrated in FIGS. 1 through 9.

Methods of using the pneumatic liquid handling circuits illustrated in FIGS. 1-10 are envisioned. The method described below is in reference to the embodiment illustrated in FIGS. 1-9. However, it can be easily adapted for use with the design illustrated in FIG. 10.

A method begins with application of sample liquid 20 to main channel 10. The driving force for flow of sample liquid 20 through main channel 10 can be capillary, gravitational, centrifugal, or can be provided by pressurized gas or a pump. It can also be provided by the source of sample liquid 20. The driving force should be sufficient to cause flow through main channel 10, but not so great as to cause flow beyond hydrophobic areas 60 and 62. A next step in the method includes the detection of sample at fill detector 30, followed by a signal from fill detector 30 to controller 90 by way of feedback loop 31. In response to the signal, heater 80 is turned on, leading to the formation of first sample bolus 20a. Once the trailing edge 21 of first sample bolus 20a has reached vent 50, heater 80 is turned off, and the concentration of analyte in the sample liquid 20 is monitored using analyte sensor 40. As sample liquid 20 reaches fill detector 30 again, a signal is sent from fill detector 30 to controller 90 by way of feedback loop 31, and heater 80 is once again turned on. As the air in gas pocket 70 expands, a second sample bolus 20b is formed, and moves toward the first sample bolus 20a and vent 50. As the second trailing edge 23 reaches vent 50, heater 80 is turned off, and the concentration of analyte in the second sample bolus 20b is determined using analyte sensor 40. This method can be repeated as necessary, and can be part of a broader monitoring method.

It will be recognized that equivalent structures may be substituted for the structures illustrated and described herein and that the described embodiment of the invention is not the only structure which may be employed to implement the claimed invention. In addition, it should be understood that every structure described above has a function and such structure can be referred to as a means for performing that function. While preferred embodiments of the present invention have been shown and described herein, it will be obvious to those skilled in the art that such embodiments are provided by way of example only. Numerous variations, changes, and substitutions will now occur to hose skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. Method of measuring the analyte concentration in a bolus of fluid using a pneumatic actuator in a fluid handling circuit, said method comprising the steps of:

positioning said fluid in a channel in said fluid handling circuit;

actuating said pneumatic actuator to inject an air into said channel when said fluid is detected by a fill detector;

injecting air from said pneumatic actuator into said channel to form an air pocket upstream from said fill detector;

forming a bolus of said fluid, said bolus having a length which is substantially equal to the distance from said fill detector to said pneumatic actuator;

moving said bolus and said air pocket through said channel until said fluid is positioned over an analyte detector in said channel;

measuring the analyte content of said bolus;

venting said air pocket from said channel.

2. A method of segregating a bolus of fluid using a pneumatic actuator in a fluid handling circuit according to claim 1 wherein said pneumatic actuator comprises:

a controller;

a pressure generator connected to said controller; and an isolator for isolating said pressure generator from said channel.

3. A method of segregating a bolus of fluid using a pneumatic actuator in a fluid handling circuit according to claim 2 wherein said pneumatic actuator further comprises:

a gas pocket connected to said channel through said isolator;

a heater controlled by said controller and adapted to heat gas in said gas pocket.

4. A method of segregating a bolus of fluid using a pneumatic actuator in a fluid handling circuit according to claim 2 wherein said pneumatic actuator further comprises:

a gas pocket connected to said channel through said isolator;

a flexible bladder connected to said gas pocket;

a plunger connected to said flexible bladder, said plunger being controlled by said controller.

* * * * *

UNITED STATES PATENT AND TRADEMARK OFFICE
CERTIFICATE OF CORRECTION

| | | |
|---|---|---|
| PATENT NO. | : 7,665,303 B2 | Page 1 of 1 |
| APPLICATION NO. | : 11/095636 | |
| DATED | : February 23, 2010 | |
| INVENTOR(S) | : Bohm et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1080 days.

Signed and Sealed this

Fourth Day of January, 2011

David J. Kappos
*Director of the United States Patent and Trademark Office*